(12) United States Patent
Yilmaz et al.

(10) Patent No.: US 12,383,712 B2
(45) Date of Patent: Aug. 12, 2025

(54) CAPACITIVE SENSOR FOR PRECISELY MEASURING HIGH STRAIN ON THE SURFACE OF A BALLOON OF A BALLOON CATHETER

(71) Applicant: BIOTRONIK AG, Bülach (CH)

(72) Inventors: Hueseyin Yilmaz, Wetzikon (CH); Jeremy Wernli, Wettingen (CH)

(73) Assignee: BIOTRONIK AG, Buelach (CH)

( * ) Notice: Subject to any disclaimer, the term of this patent is extended or adjusted under 35 U.S.C. 154(b) by 315 days.

(21) Appl. No.: 18/245,060

(22) PCT Filed: Nov. 2, 2021

(86) PCT No.: PCT/EP2021/080330
§ 371 (c)(1),
(2) Date: Mar. 13, 2023

(87) PCT Pub. No.: WO2022/096431
PCT Pub. Date: May 12, 2022

(65) Prior Publication Data
US 2023/0355936 A1    Nov. 9, 2023

(30) Foreign Application Priority Data
Nov. 9, 2020  (EP) ..................... 20206342

(51) Int. Cl.
*A61M 25/10*     (2013.01)
(52) U.S. Cl.
CPC ... *A61M 25/104* (2013.01); *A61M 2205/3327* (2013.01)

(58) Field of Classification Search
CPC .......... A61M 25/104; A61M 25/10184; A61M 2205/3327; A61M 2025/1088; A61B 5/1076; A61B 5/6853
See application file for complete search history.

(56) References Cited

U.S. PATENT DOCUMENTS

| | | | |
|---|---|---|---|
| 6,179,858 B1 * | 1/2001 | Squire | A61F 2/958 606/198 |
| 2006/0063973 A1 | 3/2006 | Makower et al. | |
| 2013/0123694 A1 | 5/2013 | Subramaniyan et al. | |
| 2019/0366057 A1 * | 12/2019 | Bihler | G01L 9/12 |
| 2021/0401375 A1 | 12/2021 | Quint | |

OTHER PUBLICATIONS

International Search Report from the corresponding International Patent Application No. PCT/EP2021/080330, dated Feb. 7, 2022.

* cited by examiner

*Primary Examiner* — Anh T Dang
(74) *Attorney, Agent, or Firm* — Greer, Burns & Crain, Ltd.; Steven P. Fallon

(57) ABSTRACT

A balloon catheter includes a balloon extending in an axial direction (z). The balloon includes an expandable balloon wall that extends around the balloon in a circumferential direction (U) and surrounds a balloon interior space of the balloon. The balloon interior space is configured to be filled with a fluid inflation medium. A capacitive sensor is configured to measure a diameter (D) extending in a radial direction (R) of the balloon. The sensor includes a capacitor having two planar and expandable electrodes arranged on the balloon wall.

15 Claims, 6 Drawing Sheets

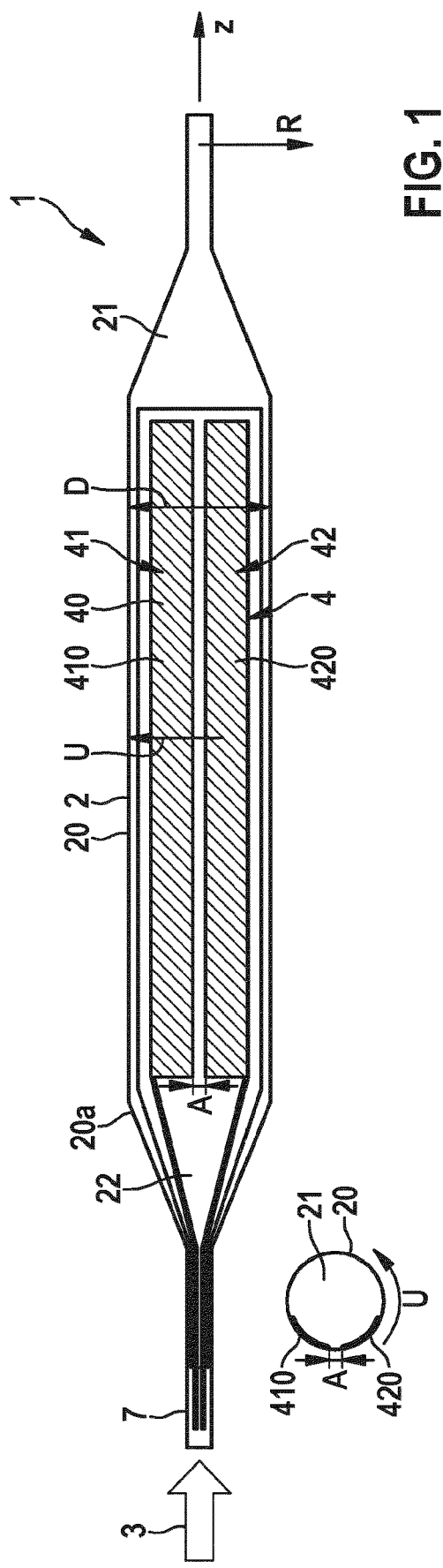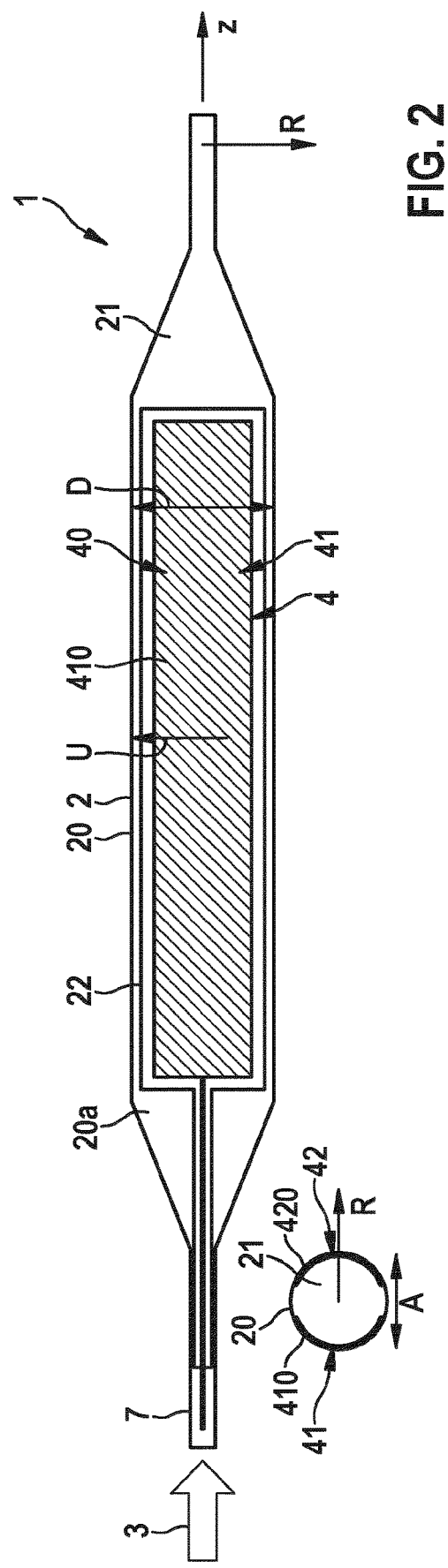

CAPACITIVE SENSOR FOR PRECISELY MEASURING HIGH STRAIN ON THE SURFACE OF A BALLOON OF A BALLOON CATHETER

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2021/080330, which was filed Nov. 2, 2021, which application claimed priority from European Application Serial Number 20206342.6, which was filed Nov. 9, 2020.

FIELD OF THE INVENTION

The invention concerns balloon catheters.

BACKGROUND

During angioplasty, the balloon of a balloon catheter is guided into the narrow region of the blood vessel to eliminate the stenosis and is inflated under high pressure (up to 16 atm) using a fluid inflation medium, which is introduced into the balloon interior space, wherein the balloon expands in particular in the radial direction (that is, perpendicularly to the axial direction of the balloon catheter), and the diameter of the balloon increases accordingly in the radial direction. As a result of the high pressure that the balloon exerts on the vessel wall, the calcium deposits in the stenosis are pushed into the vessel wall, and the vessel diameter increases accordingly. During such a procedure, it is desirable for the treating physician to be able to monitor or set the diameter of the balloon that arises (in the radial direction) during inflation of the balloon in a manner that is as controlled and efficient as possible.

Strain measurements using a resistive principle (change in electrical resistance during expansion) are known in this regard from the prior art.

U.S. Pat. No. 8,585,594 furthermore discloses a heart valve including eight elongated conductors, so that a capacitance can be determined between each pair of conductors.

Furthermore, U.S. Pat. No. 6,179,858 discloses a field of capacitive sensors, which each include two electrically conductive pads connected to an inflatable balloon, wherein the dimensions of the respective pad remain unchanged when the balloon is expanded in the circumferential direction. The pads can be made of an aluminum film, for example.

Disadvantages with almost all resistive strain sensors for high strain include undesirable effects, such as drift or hysteresis during repeated measurements, as well as a strongly non-linear relationship of the sensor signal to the strain. The reasons for this disadvantageous behavior are related to the morphology of the special conducting and highly expandable materials, which are often based on metal nanoparticles and used here.

If the balloon diameter is to be determined by way of capacitive sensors at very high strain (for example, 30%), the large increase in volume of the balloon has to be taken into account in the conductor or electrode design, which often necessitates a complex electrode design.

SUMMARY OF THE INVENTION

A preferred balloon catheter includes a sensor, which has a comparatively simple design and allows the diameter of the balloon to be measured even under high strain of the balloon wall. In particular, the sensor should not have any drift during cyclical loading, and no hysteresis. A preferred balloon catheter includes a balloon extending in an axial direction. An expandable balloon extends around the balloon in a circumferential direction and surrounds an interior space of the balloon. The balloon interior space can be filled with a fluid inflation medium for inflating the balloon. A capacitive sensor configured to determine a diameter of the balloon extends in a radial direction of the balloon.

BRIEF DESCRIPTION OF THE DRAWINGS

Embodiments of the invention and further features and advantages of the invention will be described hereafter based on the figures. In the drawings:

FIG. 1 shows a schematic representation of an embodiment of a balloon catheter according to the invention, including adjoining electrodes or fingers in the circumferential direction of the balloon;

FIG. 2 shows a schematic representation of another embodiment of a balloon catheter according to the invention, including electrodes or fingers opposing each other in the radial direction of the balloon;

DETAILED DESCRIPTION OF THE PREFERRED EMBODIMENTS

Figure 3:
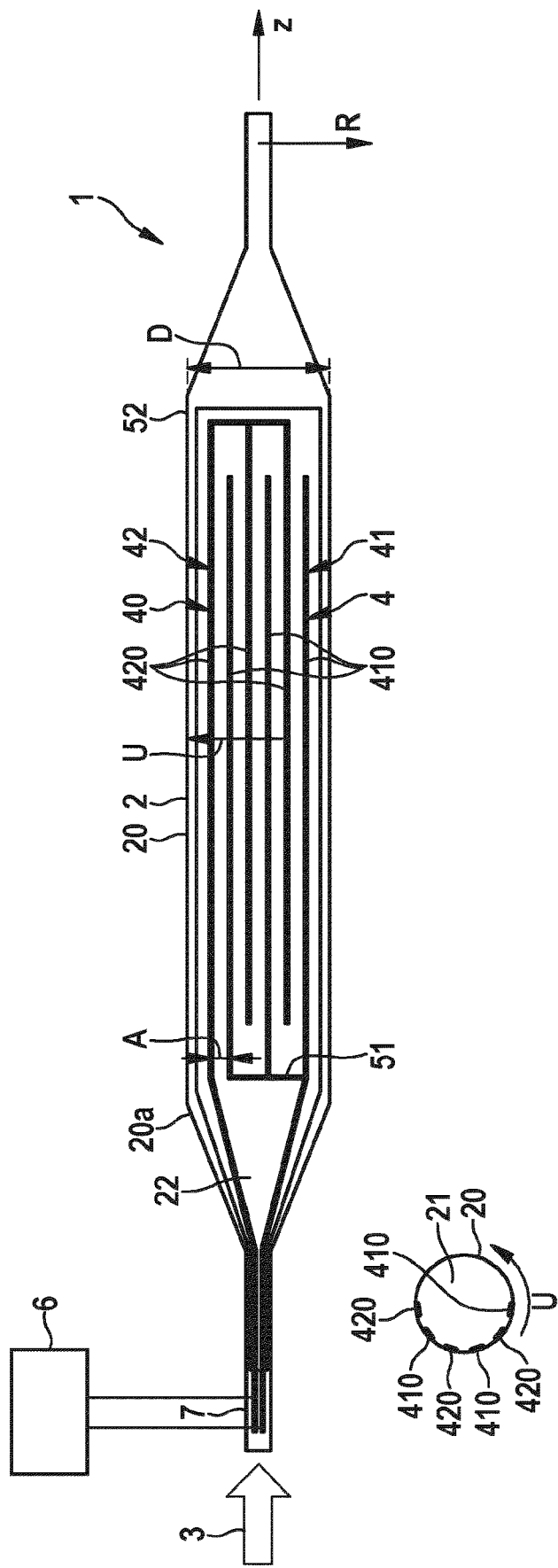
FIG. 3 shows a schematic representation of another embodiment of a balloon catheter according to the invention, including two electrodes that include fingers engaging each other (finger capacitor)

A preferred sensor includes a capacitor including two planar and expandable electrodes, which are each fixed on the balloon wall. Planar electrodes or fingers (see below) shall in particular be understood to mean that the electrodes or fingers (see below) have a thickness normal to the balloon wall which is smaller than expansions of the electrodes or fingers in the two spatial directions perpendicular to the thickness.

According to one embodiment, the electrodes are preferably arranged on an outside of the balloon wall and are preferably covered by an electrically insulating layer.

According to one embodiment of the balloon catheter, it is provided that a distance between the electrodes increases when the balloon is being inflated and/or that a surface area of the particular electrode increases during inflation.

According to one embodiment of the balloon catheter, it is furthermore provided that the distance and the surface areas increase in such a way that a capacitance of the capacitor changes, and in particular increases, when the balloon is being inflated.

According to one embodiment of the balloon catheter, it is furthermore provided that each electrode includes at least one planar finger that extends longitudinally in the axial direction of the balloon. The fingers preferably extend parallel to one another when the balloon is inflated.

Within the scope of the present application, an electrode in the form of a finger shall be understood to mean a planar electrode taking up a surface area along the balloon surface, wherein the expansion along the longitudinal balloon axis is longer than the expansion along the balloon circumference.

According to one embodiment, it is preferably provided that the respective finger extends over at least 30%, in particular over at least 50%, in particular over at least 60%, in particular over at least 70%, in particular over at least 80%, in particular over at least 90% of the length of the balloon in the axial direction.

According to one embodiment of the balloon catheter, it is furthermore provided that the fingers of the two electrodes are arranged adjoining one another on the same balloon half in the circumferential direction of a balloon, when the balloon is inflated.

Arranged in an adjoining manner on the same balloon half shall be understood to mean that the centers of the surface areas form an angle of less than 180° with the catheter axis.

Preferably, the centers of the surface areas of the fingers form an angle of less than 90°, and in particular less than 45°, with the catheter axis.

According to one embodiment of the invention, it is provided that the aforementioned distance between the electrodes, in particular between the fingers of the electrodes, extends in the circumferential direction of a balloon or perpendicularly to the axial direction of a balloon, when the balloon is inflated.

According to an alternative embodiment of the balloon catheter, it is provided that the fingers of the two electrodes are arranged opposite one another in the radial direction of a balloon (that is on different balloon halves), when the balloon is inflated. Arranged opposite one another shall be understood to mean that the centers of the surface areas form an angle of 180° with the catheter axis.

Here, it is provided according to one embodiment that the aforementioned distance between the two electrodes, in particular between the fingers, extends in the radial direction of the balloon, when the balloon is inflated.

According to one embodiment of the invention, it is furthermore provided that the fingers of the electrodes together preferably cover 2% to 95% of the outside of the balloon, referred to an inflated state of the balloon. The fingers of the electrodes together preferably cover between 2% and 50%, in particular 5% to 25%, in particular 10% to 20%, of the outside of the balloon. In particular, it can be expedient for the fingers to overall extend across at least 5%, in particular across at least 10%, in particular across at least 20%, in particular across at least 30%, in particular across at least 50%, and in particular across at least 70% of the outer surface of the balloon.

According to a further embodiment of the invention, it is provided that each electrode includes multiple planar fingers extending longitudinally in the axial direction of the balloon, wherein the fingers preferably extend parallel to one another when the balloon is inflated.

In the case of multiple fingers per electrode, it is preferably provided according to one embodiment of the invention that the fingers of the two electrodes engage into each other. This means, in particular, that each electrode includes one or more fingers, wherein the respective finger protrudes into a gap of the other electrode which extends between two adjoining fingers.

According to one embodiment, it is furthermore provided in the case of the fingers engage into each other that the fingers of each electrode extend from a planar base of the respective electrode, wherein the two bases extend in the circumferential direction of the balloon, when the balloon is inflated. The respective base preferably extends perpendicularly to the fingers connected (preferably integrally) thereto, and connects these to one another in an electrically conducting manner.

According to one embodiment of the invention, it is furthermore provided that the two bases, when the balloon is inflated, are located opposite one another in the axial direction of the balloon and/or that the two bases, when the balloon is inflated, are arranged offset from one another in the circumferential direction of the balloon, in particular so as to enable the engagement of the fingers into each other.

According to one embodiment, the electrodes or fingers or bases of the sensors are made of an electrically conductive as well as expandable material, in particular electrically conductive ink, which can be printed onto the outside of the balloon wall or balloon material, for example.

According to one embodiment of the invention, it is furthermore provided that the sensor includes an evaluation unit, which is connected to the two electrodes in an electrically conducting manner, wherein the evaluation unit is designed to measure the capacitance of the capacitor and to use it for determining the diameter of the balloon.

For inflation or deflation, the balloon catheter preferably includes a catheter shaft, wherein the balloon is connected to a distal end of the catheter shaft, and wherein the catheter shaft surrounds a lumen which is connected to the balloon interior space and via which the inflation medium can be introduced into the balloon interior space.

According to a further aspect of the invention, a method for measuring a diameter of a balloon is described, using a balloon catheter according to the invention, including the following steps:
inflating the balloon by introducing a fluid inflation medium into the balloon interior space; and
measuring the capacitance of the capacitor, and automatically calculating the diameter of the balloon, using the measured capacitance.

According to one embodiment of the method, it is provided that an outwardly facing surface of the balloon is increased by 10% to 20%, by 25%, by 30% when the balloon is inflated compared to the deflated state of the balloon. The surface area of the electrodes increases to the same degree.

FIGS. 1 to 3 show different embodiments of a balloon catheter 1 according to the invention, which can be used, for example, to carry out angioplasty.

The balloon catheter 1 includes a balloon 2 extending in an axial direction z, which includes an expandable balloon wall 20 that extends around the balloon 2 in a circumferential direction U and surrounds a balloon interior space 21 of the balloon 2, wherein the balloon interior space 21 can be filled with a fluid inflation medium 3 for inflating the balloon 2. The balloon catheter 1 furthermore includes a capacitive sensor 4 for determining a diameter D extending in a radial direction R of the balloon 2, wherein the sensor 4 includes a capacitor including two planar and expandable electrodes 41, 42, which are arranged on the balloon wall 20 in each case or are fixed there.

Figure 4A:
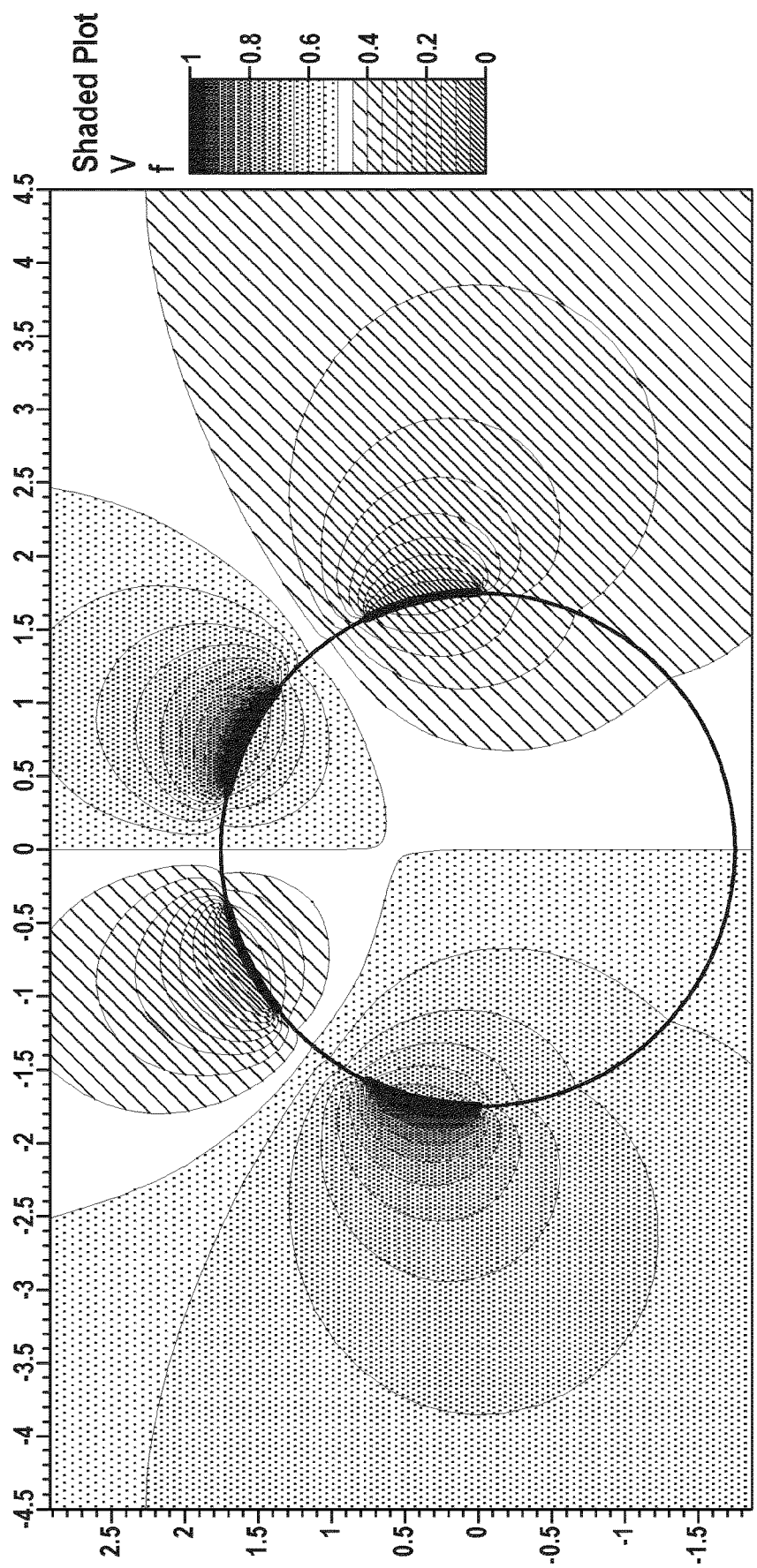
FIG. 4A shows a 2-dimensional electrostatic simulation of the change in capacitance of an embodiment of a finger capacitor, including four fingers (two per electrode) in the normal state.
Figure 4B:
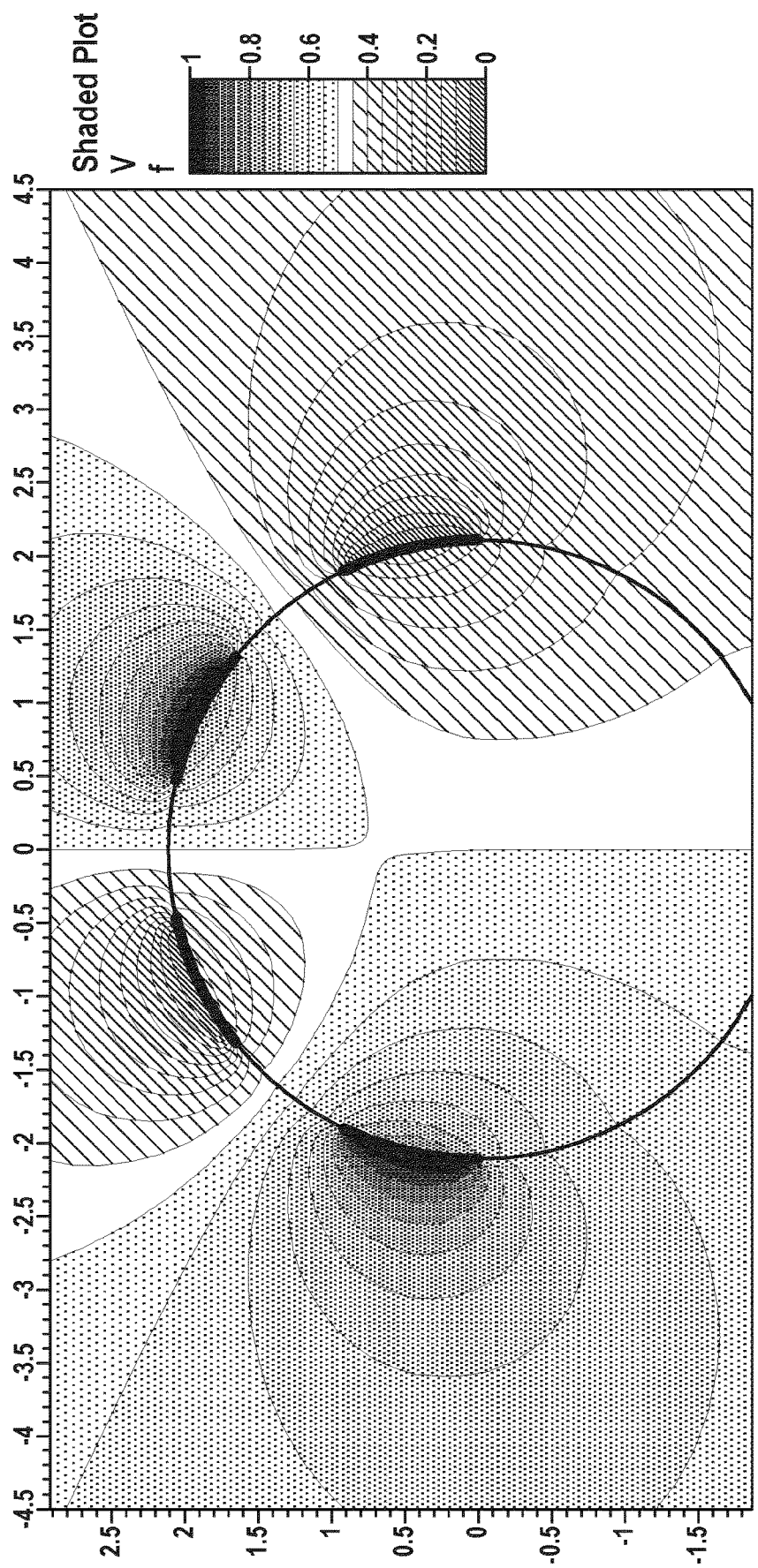
FIG. 4B shows the balloon according to FIG. 4A in the inflated state and radially expanded by 20%. The capacitance increases from approximately 25 pF (FIG. 4A) to 29 pF (model assumptions: volume constancy; media in the balloon interior space: NaCl solution; medium outside the balloon: air)

When the balloon 2 is inflated, the diameter D thereof increases. The expandable sensor 4 on the surface or outside 20a of the balloon wall 20 follows this radial expansion, whereby the capacitance thereof changes (see, for example, FIGS. 4A and 4B). In the process, both the surface area of the conducting structures 41, 42 and a distance A therebetween increase, whereby these two effects overlap: A pure increase in the distance A between the electrodes 41, 42 ensures a decrease in capacitance, while the increase in surface area of the electrodes 41, 42 due to the expansion ensures an increase in capacitance. A net increase in capacitance can be observed with increasing balloon diameter D both during the simulation (FIGS. 4A and 4B) and during practical testing (see FIG. 5A). The latter additionally show good reproducibility of the capacitive sensor signal for the separately measured balloon diameter D during multiple inflation cycles (see test set-up FIG. 5B).

Different exemplary embodiments are conceivable, from a finger capacitor design including multiple fingers 410, 420 per electrode 41, 42, to a reduced number of one finger 410, 420 per electrode 41, 42. The conducting structures 41, 42 can be applied to only half the circumference of the balloon cylinder, that is, to the same balloon half, or to the entire circumference thereof.

The electrodes 41, 42 or fingers 410, 420 of the sensor 4 or capacitor 40 are preferably made of an expandable electrically conductive material. The material can, for example, be an expandable, conducting silver paste or the like (such as PE874 from DuPont, which is based on metal nanoparticles). Such a material, which is usually ink-like/paste-like, is applied onto the surface or outside 20a of the balloon using suitable printing technology (such as screen printing, micropenning, ink jet or the like), depending on viscosity, and is also heat-treated there (referred to as "curing"), if necessary.

In detail, FIG. 1 shows an embodiment of the balloon catheter 1 in which the two electrodes 41, 42 in the form of longitudinally extending, planar (in particular rectangular) fingers 410, 420 extend in the axial direction z of the balloon 2, and are arranged adjoining one another in the circumferential direction U, that is, on the same balloon half or side of the balloon 2.

FIG. 2, in contrast, shows an alternative arrangement of the electrodes 41, 42, wherein here as well the electrodes 41, 42 are designed as longitudinally extending, planar (in particular rectangular) fingers 410, 420, which now, however, are arranged on opposite halves of the balloon 2, that is, are located opposite one another in the radial direction of the balloon R.

FIG. 3 shows another alternative embodiment, wherein, in contrast to FIGS. 1 and 2, each electrode 41, 42 of the sensor 4 or capacitor 40 of the balloon 2 includes multiple planar ringers 410, 420 longitudinally extending in the axial direction z of the balloon 2.

There, the fingers 410, 420 of the two electrodes 41, 42 are arranged in an engagement to each other, that is in particular that each electrode 41, 42 includes one or more fingers 410, 420, wherein the respective finger 410 (or 420) of the one electrode 41 (or 42) protrudes into a gap of the other electrode 42 (or 41) extending between two adjoining fingers 420 (or 410). Such a capacitor 40 is also referred to as a finger capacitor.

In particular, it is provided that the fingers 410, 420 of each electrode 41, 42 extend from a planar base 51, 52 of the particular electrode 41, 42, wherein the two bases 51, 52 extend in the circumferential direction U of a balloon 2 when the balloon 2 is inflated, and are arranged offset from one another with respect to the circumferential direction U, so that the parallel fingers 410, 410 can engage to each other.

In FIGS. 1 to 3, the fingers 410, 420 or electrodes 41, 42 are in each case applied onto an outside 20a of the balloon wall 20, in particular printed on, and are in each case preferably covered with an electrically insulating layer 22.

Figure 5A:
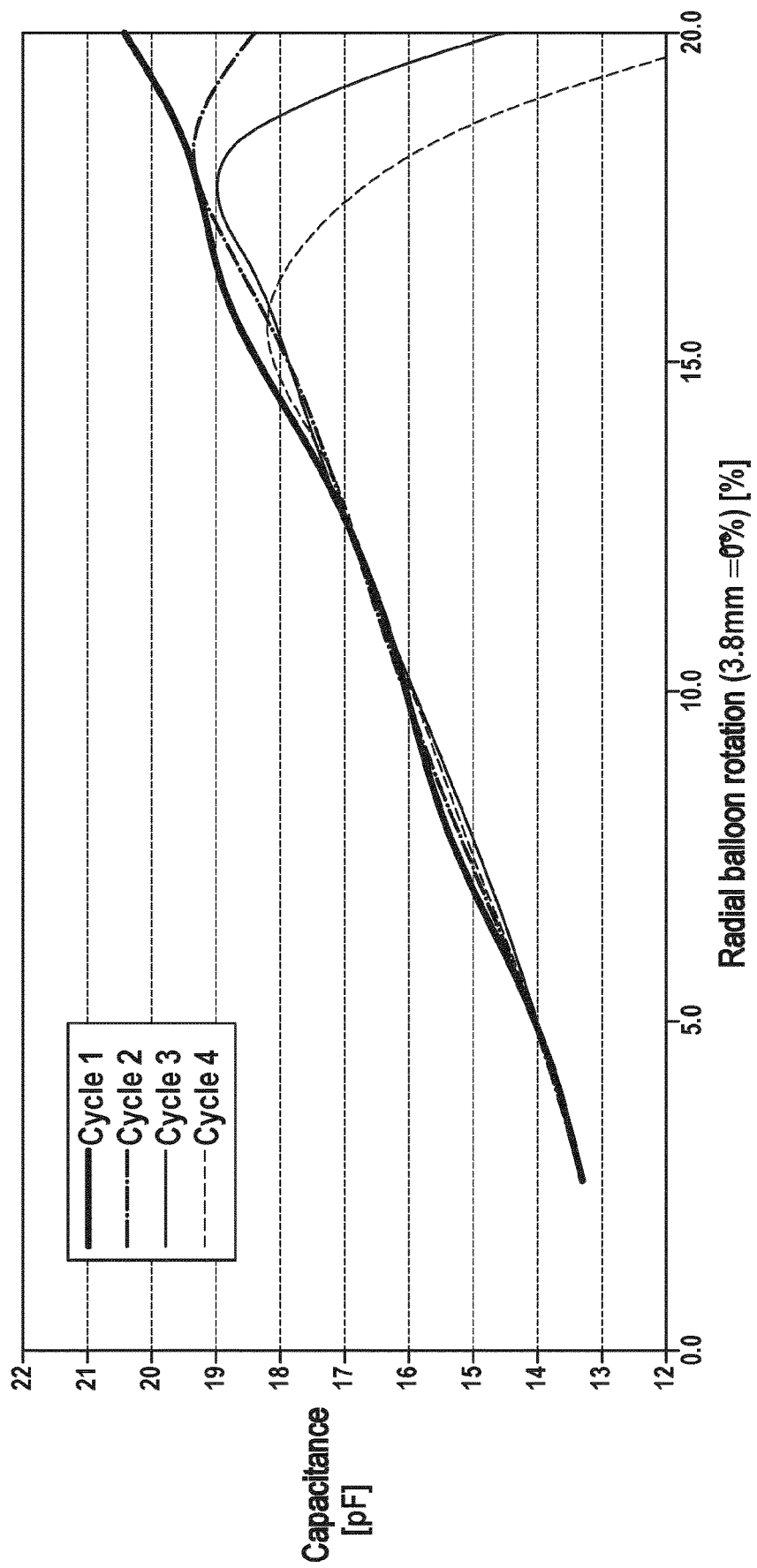
FIG. 5A shows measurement results of an embodiment of a finger capacitor including six fingers (three fingers per electrode) on the balloon, wherein the measured change in capacitance during radial balloon expansion is substantially linear and reproducible over the measured four inflation cycles.
Figure 5B:
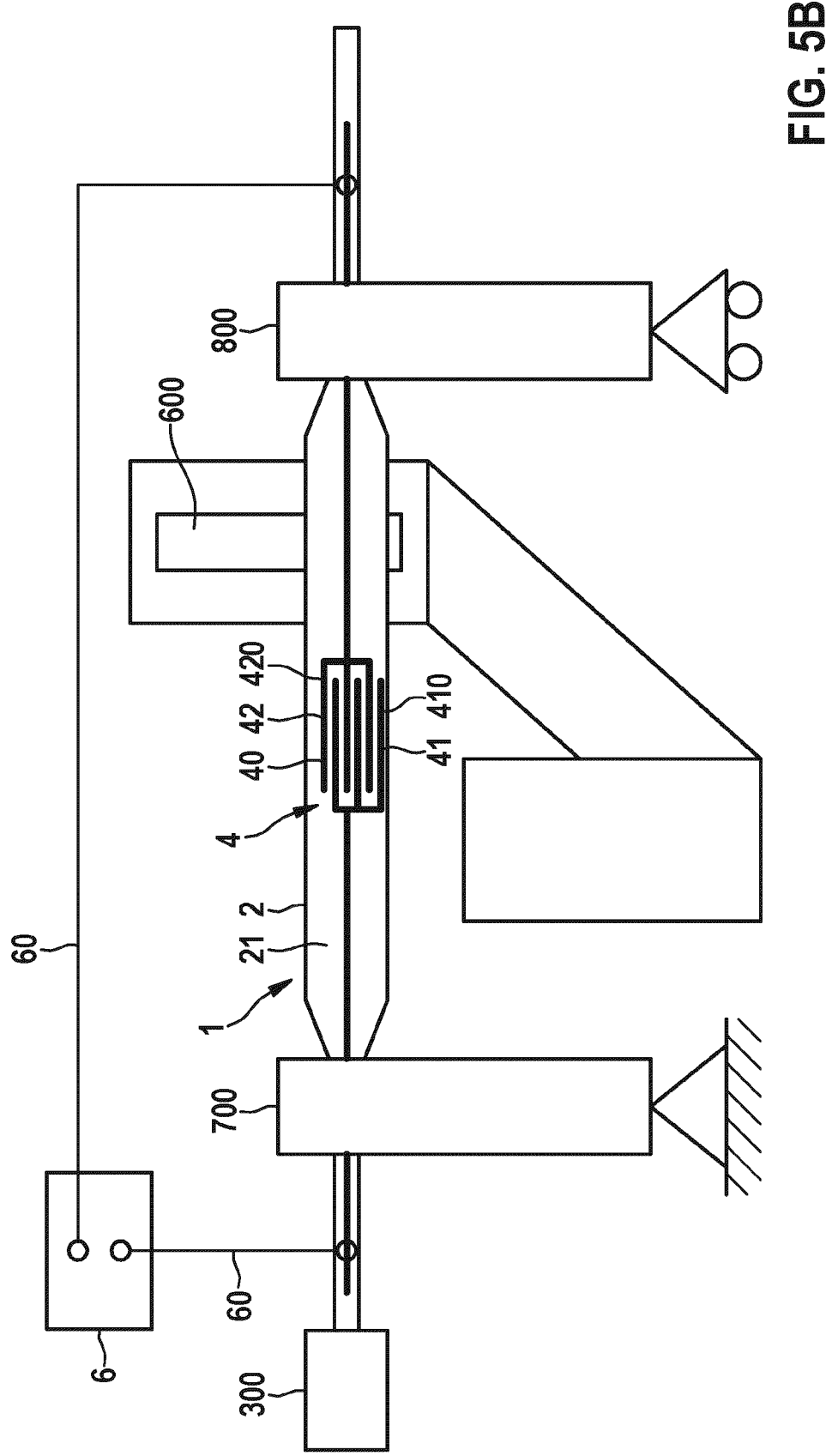
FIG. 5B shows a schematic measuring set-up for carrying out the measurements according to FIG. 5A, with simultaneous capacitance measurement by way of an LCR meter (evaluation unit) and diameter measurement by way of an optical sensor.

FIG. 5A shows measurement results achieved by way of the test set-up according to FIG. 5B. In the process, a balloon catheter 1 including a capacitor 40 was used, the electrodes 41, 42 of which include three fingers 410, 420, respectively. The measured change in capacitance during radial balloon expansion is substantially linear and reproducible over the measured four inflation cycles.

According to FIG. 5B, the balloon 2 of the balloon catheter 1 is held by way of a fixed balloon mount 700 and an axially floating balloon mount 800 for measuring the results according to FIG. 5A. Using an LCR meter 6 and an optical sensor 600, the capacitance of the capacitor 40 of the sensor 4 and the associated diameter D are measured. The electrodes 41, 42 are connected to the evaluation unit 6 via electrical lines 60 for this purpose. The pressure in the balloon interior space 21 can be measured by way of a pressure tester 300. A NaCl solution (serving as the inflation medium) can be added to the balloon interior space 21, for example, for inflating the balloon 2.

Compared to a resistive strain sensor, the capacitive strain sensor 4 according to the invention advantageously has a linear behavior of the sensor signal to strain and has virtually no hysteresis or drift.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims

The invention claimed is:
1. A balloon catheter comprising:
a balloon extending in an axial direction (z), the balloon comprising an expandable balloon wall that extends around the balloon in a circumferential direction (U) and surrounds a balloon interior space of the balloon, wherein the balloon interior space is configured to be filled with a fluid inflation medium; and
a capacitive sensor configured to determine a diameter (D) of the balloon, the sensor extending in a radial direction (R) of the balloon, wherein the sensor comprises a capacitor, the capacitor comprising two planar and expandable electrodes, each being arranged on the balloon wall, wherein each of the two planar and expandable electrodes each comprises a planar base that extends in the circumferential direction (U) of the balloon when the balloon is inflated and at least two planar fingers that extend from the planar base longitudinally in the axial direction (z) of the balloon, wherein the at least one of the two planar fingers of one of the planar and expandable electrodes protrudes into a gap between the at least two planar fingers of the other of the planar and expandable electrodes.

2. The balloon catheter according to claim 1, wherein the capacitor is configured and arranged such that a distance (A) defined by the gaps increases with inflation of the balloon and/or that a surface area of one or both of the electrodes increases with inflation of the balloon.

3. The balloon catheter according to claim 2, wherein the electrodes are configured to have a changing capacitance as a function of balloon inflation.

4. The balloon catheter according to claim 2, wherein the at least two planar fingers of each of the electrodes are configured to extend across at least 30% of a length of the balloon in the axial direction (z).

5. The balloon catheter according to claim 4, wherein the at least two planar fingers of each of the electrodes is configured to extend across at least 70% of the length of the balloon in the axial direction (z).

6. The balloon catheter according to claim 4, wherein the at least one planar electrode of each of the electrodes is configured to extend across at least 90% of the length of the balloon in the axial direction (z).

7. The balloon catheter according to claim 2, wherein the at least two planar fingers of one of the electrodes are arranged to protrude into the gaps of the at least two planar fingers of the other of the electrodes on a same balloon half in the circumferential direction (U) of the balloon when the balloon is inflated.

8. The balloon catheter according to claim 2, wherein said distance (A) extends in the circumferential direction (U) of the balloon when the balloon is inflated.

9. The balloon catheter according to claim 2, wherein the at least two planar fingers of one of the electrodes and the at least two planar fingers of the other of the electrodes are arranged opposite one another in the radial direction (R) of the balloon when the balloon is inflated.

10. The balloon catheter according to claim 2, wherein said distance (A) extends in the radial direction (R) of the balloon when the balloon is inflated.

11. The balloon catheter according to claim 2, wherein the at least two planar fingers of one of the electrodes and the at least two planar fingers of the other of the electrodes together cover 2% to 95%, of an outside of the balloon wall in an inflated state of the balloon.

12. The balloon catheter according to claim 2, wherein the bases of the electrodes are located opposite one another in the axial direction (z) of the balloon when the balloon is inflated, and are arranged offset from one another in the circumferential direction (U) of the balloon when the balloon is inflated.

13. A method for measuring a diameter (D) of a balloon, using a balloon catheter according to claim 1, comprising the following steps:
inflating the balloon by introducing a fluid inflation medium into the balloon interior space; and
measuring the capacitance of the capacitor, and automatically calculating the diameter (D) of the balloon using the measured capacitance.

14. A balloon catheter comprising:
a balloon extending in an axial direction (z), the balloon comprising an expandable balloon wall that extends around the balloon in a circumferential direction (U) and surrounds a balloon interior space of the balloon, wherein the balloon interior space is configured to be filled with a fluid inflation medium; and
a capacitive sensor configured to determine a diameter (D) of the balloon, the sensor extending in a radial direction (R) of the balloon (2), wherein the sensor comprises a capacitor, the capacitor comprising two planar and expandable electrodes, each being arranged on the balloon wall, wherein each of the electrodes comprises at least one planar finger longitudinally extending in the axial direction (z) of the balloon, wherein the at least one planar finger of one of the electrodes and the at least one planar finger of the other of the electrodes together cover between 5% to 25% of the outside of the balloon wall in the inflated state of the balloon.

15. A balloon catheter comprising:
a balloon extending in an axial direction (z), the balloon comprising an expandable balloon wall that extends around the balloon in a circumferential direction (U) and surrounds a balloon interior space of the balloon, wherein the balloon interior space is configured to be filled with a fluid inflation medium; and
a capacitive sensor configured to determine a diameter (D) of the balloon, the sensor extending in a radial direction (R) of the balloon (2), wherein the sensor comprises a capacitor, the capacitor comprising two planar and expandable electrodes, each being arranged on the balloon wall, wherein each of the electrodes comprises at least one planar finger longitudinally extending in the axial direction (z) of the balloon, wherein the at least one planar finger of one of the electrodes and the at least one planar finger of the other of the electrodes together cover between 10% to 20% of the outside of the balloon wall in the inflated state of the balloon.

\* \* \* \* \*